(12) United States Patent
Ohara

(10) Patent No.: US 10,120,154 B2
(45) Date of Patent: Nov. 6, 2018

(54) OPTICAL FIBER LENGTH ADJUSTER

(71) Applicant: OLYMPUS CORPORATION, Tokyo (JP)

(72) Inventor: Satoshi Ohara, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 799 days.

(21) Appl. No.: 14/561,467

(22) Filed: Dec. 5, 2014

(65) Prior Publication Data

US 2015/0079218 A1 Mar. 19, 2015

Related U.S. Application Data

(63) Continuation of application No. PCT/JP2013/064105, filed on May 21, 2013.

(30) Foreign Application Priority Data

Jun. 7, 2012 (JP) .................................. 2012-129747

(51) Int. Cl.
*G02B 6/44* (2006.01)
*B29D 11/00* (2006.01)
(Continued)

(52) U.S. Cl.
CPC ........ *G02B 6/4457* (2013.01); *A61B 1/00165* (2013.01); *A61B 1/07* (2013.01); *B29D 11/00663* (2013.01); *G02B 6/444* (2013.01); *G02B 23/2476* (2013.01); *B29K 2105/253* (2013.01)

(58) Field of Classification Search
CPC .. G02B 6/4457; G02B 6/444; G02B 23/2476; B29D 11/00663; A61B 1/00165; A61B 1/07; B29K 2105/253
See application file for complete search history.

(56) References Cited

U.S. PATENT DOCUMENTS 5,268,986 A    12/1993  Kakii et al.
5,894,540 A *   4/1999  Drewing ................ G02B 6/444
                                                385/135

(Continued)

FOREIGN PATENT DOCUMENTS

CN    102135651 A     7/2011
JP    H05-303018 A   11/1993
(Continued)

OTHER PUBLICATIONS

Extended Supplementary European Search Report dated Dec. 17, 2015 from related European No. 13 80 0187.0.
(Continued)

*Primary Examiner* — Ryan Lepisto
(74) *Attorney, Agent, or Firm* — Scully, Scott, Murphy & Presser, P.C.

(57) ABSTRACT

An optical fiber length adjuster includes an entrance and an exit 16 for an optical fiber, and a holding portion to hold the optical fiber so that the optical fiber is deformed. The holding portion is configured to decrease the length of the part of the optical fiber that is held, when tensile force applied to the optical fiber is increased, and increase the length of the part of the optical fiber that is held, when the tensile force applied to the optical fiber is decreased.

12 Claims, 5 Drawing Sheets

(51) Int. Cl.
*A61B 1/07* (2006.01)
*G02B 23/24* (2006.01)
*A61B 1/00* (2006.01)
*B29K 105/00* (2006.01)

(56) References Cited

U.S. PATENT DOCUMENTS

| | | | | |
|---|---|---|---|---|
| 6,361,360 | B1* | 3/2002 | Hwang | G02B 6/4457 |
| | | | | 385/135 |
| 7,206,076 | B2* | 4/2007 | Blalock | G01B 11/0691 |
| | | | | 356/479 |
| 8,358,898 | B2* | 1/2013 | Ayme | G02B 6/4457 |
| | | | | 385/135 |
| 2005/0151977 | A1 | 7/2005 | Blalock | |
| 2006/0024015 | A1* | 2/2006 | Arima | G02B 6/4457 |
| | | | | 385/135 |
| 2008/0228033 | A1* | 9/2008 | Tumlinson | A61B 1/00096 |
| | | | | 600/112 |

FOREIGN PATENT DOCUMENTS

| | | |
|---|---|---|
| JP | H10-079542 A | 3/1998 |
| JP | 2000-298010 A | 10/2000 |
| JP | 2002-258124 A | 9/2002 |
| JP | 2006-030682 A | 2/2006 |
| JP | 4732783 B2 | 7/2011 |

OTHER PUBLICATIONS

Japanese Office Action dated Mar. 22, 2016 from related Japanese Patent Application No. 2012-129747, together with an English language translation.
International Search Report dated Jul. 2, 2013 issued in PCT/JP2013/064105.
English Abstract of JP 2006-296656 A, dated Nov. 2, 2006.
English translation of International Preliminary Report on Patentability together with the Written Opinion dated Dec. 18, 2014 received in related International Application No. PCT/JP2013/064105.

* cited by examiner

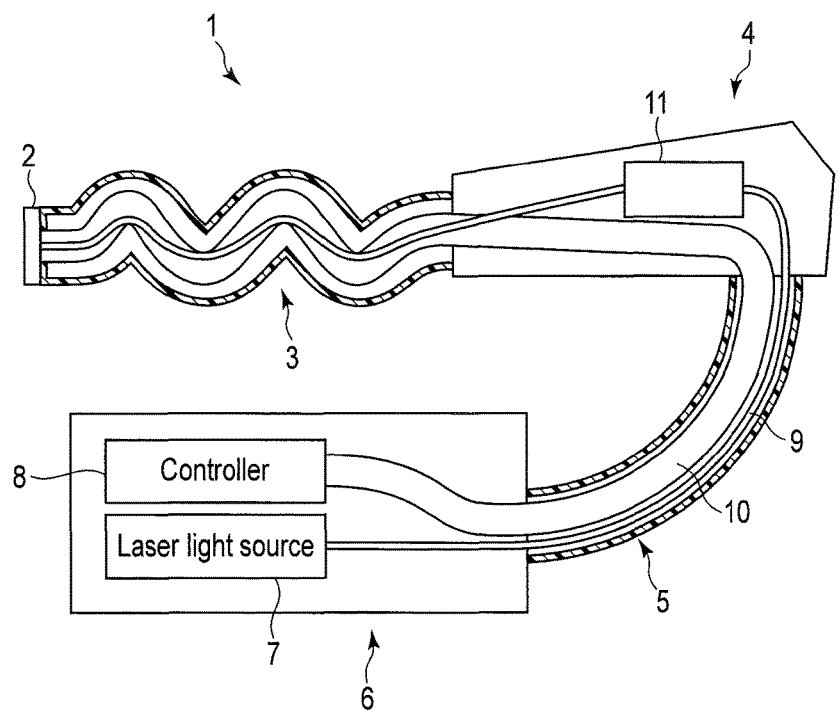
F I G. 1
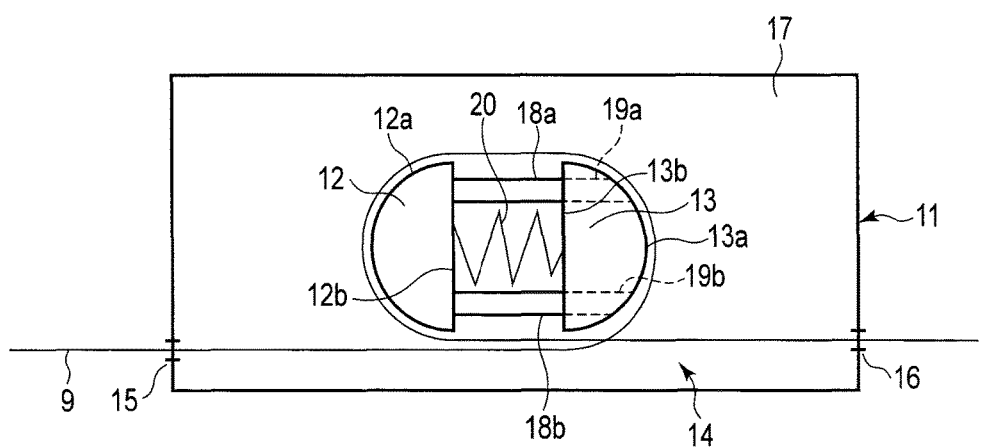
F I G. 2

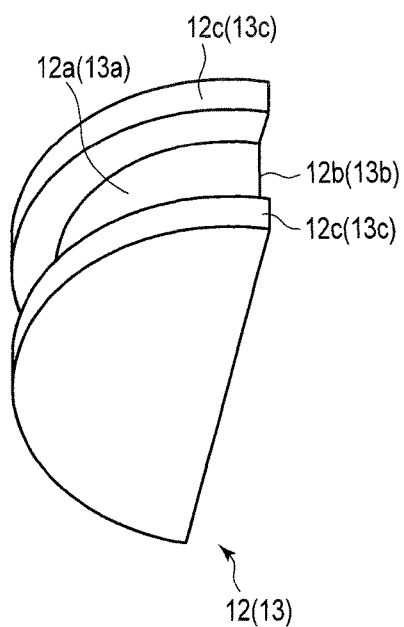
F I G. 3
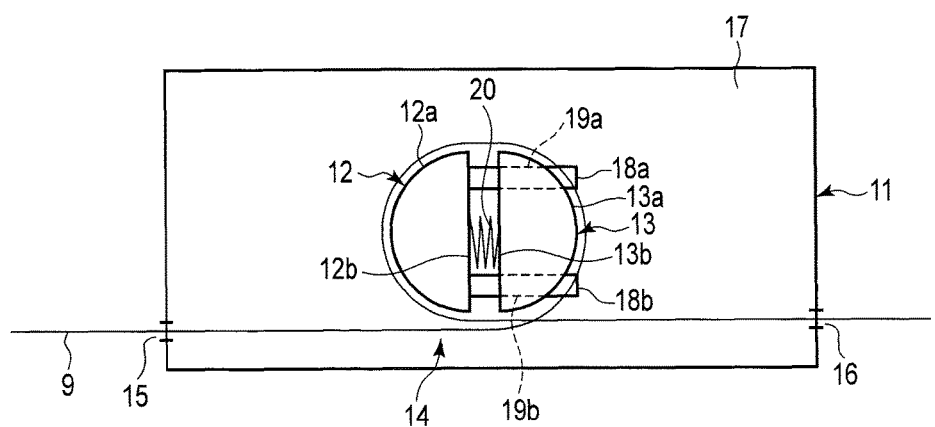
F I G. 4

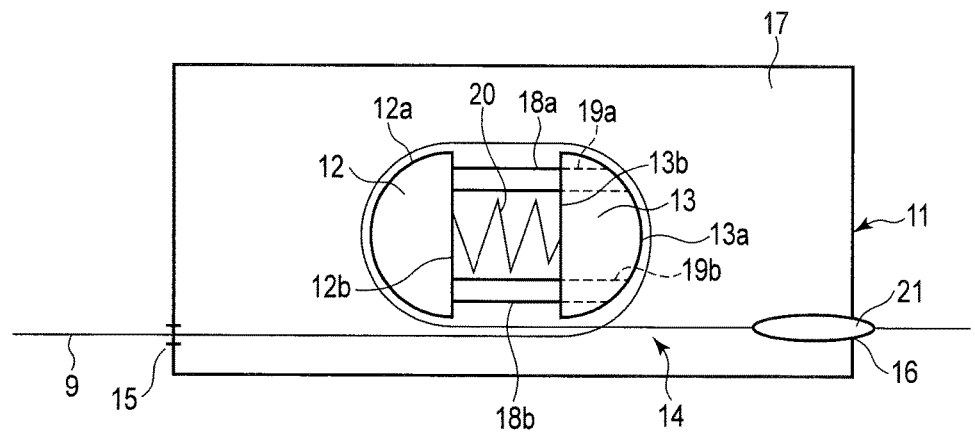
F I G. 5
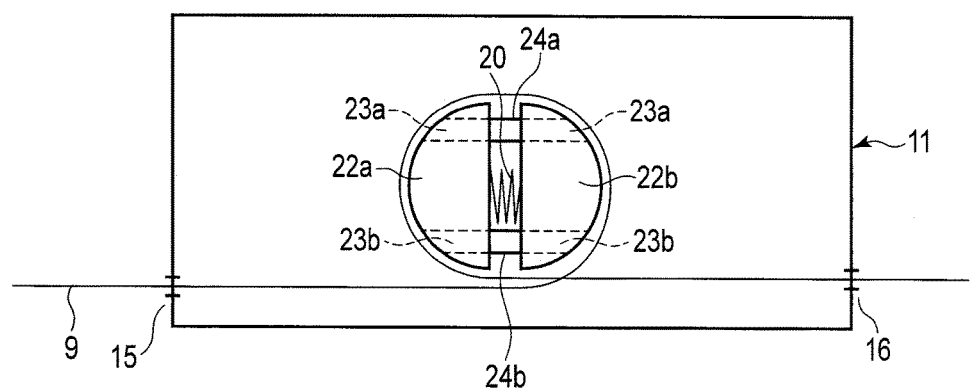
F I G. 6

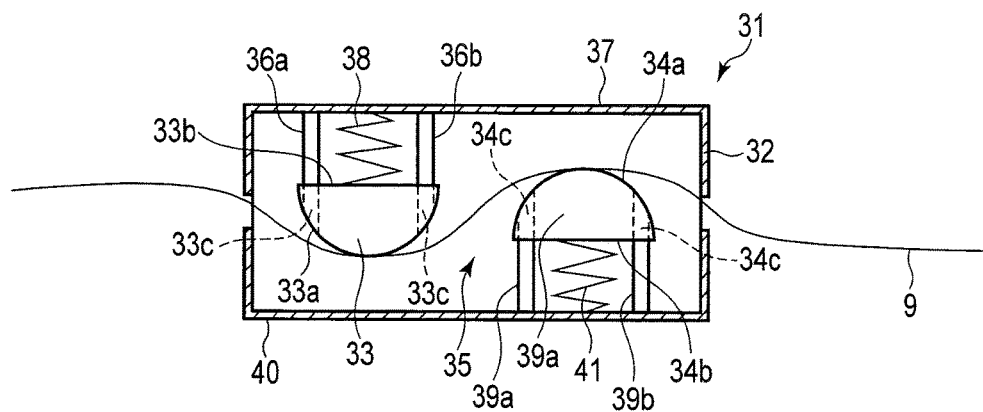
F I G. 7
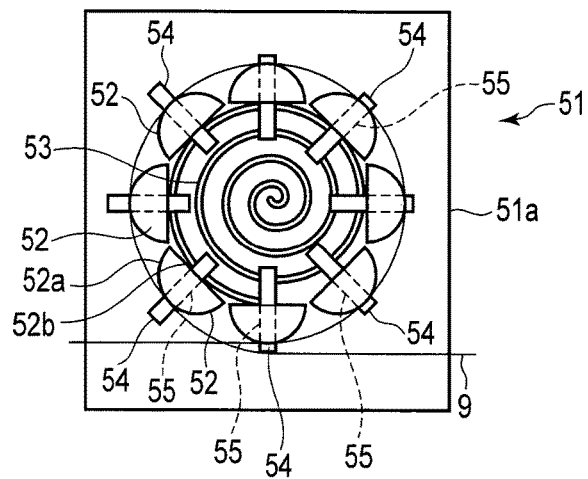
F I G. 8

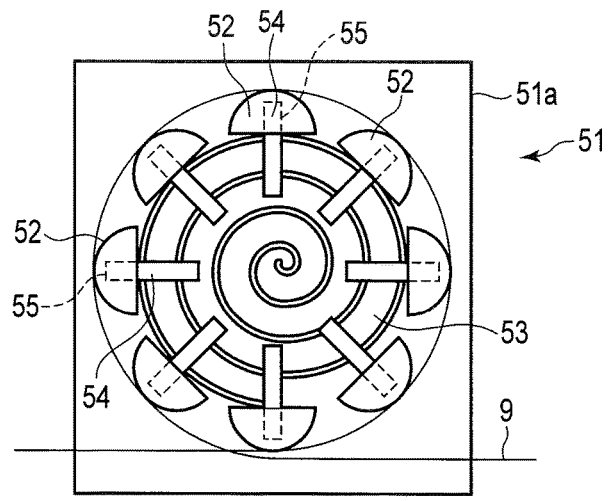
F I G. 9
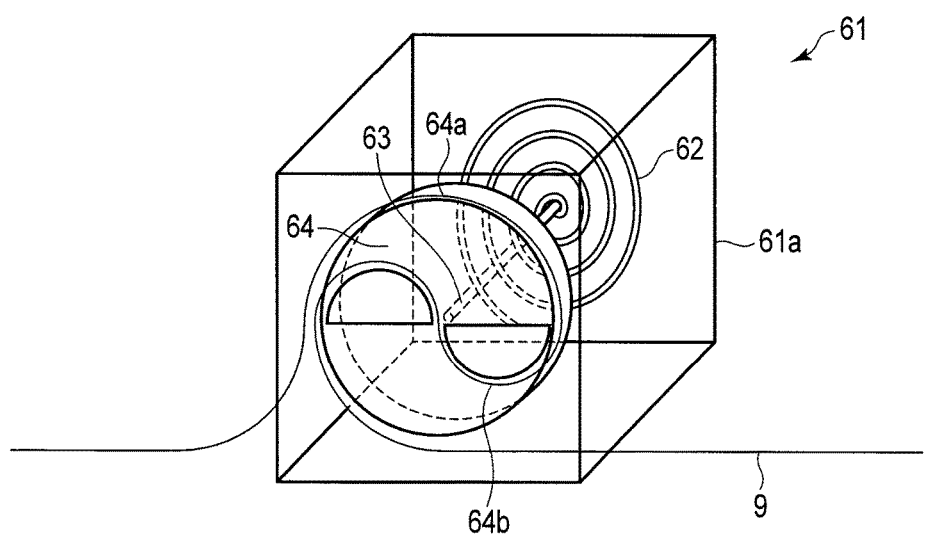
F I G. 10

OPTICAL FIBER LENGTH ADJUSTER

CROSS-REFERENCE TO RELATED APPLICATIONS

This application is a Continuation application of PCT Application No. PCT/JP2013/064105, filed May 21, 2013 and based upon and claiming the benefit of priority from prior Japanese Patent Application No. 2012-129747, filed Jun. 7, 2012, the entire contents of all of which are incorporated herein by reference.

BACKGROUND OF THE INVENTION

1. Field of the Invention

The present invention relates to an optical fiber length adjuster to be attached to a device having an optical fiber therein and adjust the length of the optical fiber.

2. Description of the Related Art

There has heretofore been a device having an optical fiber therein such as an endoscope. In the endoscope, a light source is connected to a proximal end side of an elongated insertion portion to be inserted into the body or lumen of an observation target. Light from the light source is guided by the optical fiber from the light source outside the endoscope to the distal end of the insertion portion of the endoscope.

On the other hand, a body insertion portion of a medical flexible endoscope is designed to be sufficiently curvable. In the actual insertion into the body as well, the distal end of the endoscope is inserted into the body while the insertion portion is curved. When an optical fiber is incorporated in this curvable insertion portion of the endoscope, the necessary length of the optical fiber differs between the curved state of the endoscope insertion portion and the straight state (uncurved state) of the endoscope insertion portion. For example, when the endoscope insertion portion is in the straight state, the necessary length of the optical fiber is smallest. In contrast, when the endoscope insertion portion is curved, the length of the optical fiber is greater than in the straight state. Therefore, tensile force is applied to the optical fiber when the length of the optical fiber incorporated in the insertion portion of the endoscope is smaller the necessary length. When the length of the optical fiber incorporated in the insertion portion of the endoscope is greater than the necessary length, the optical fiber is superfluous, and the optical fiber may buckle in the middle part.

Japanese Patent No. 4732783 shows an endoscope having the following configuration. One optical fiber is incorporated in an insertion portion of the endoscope. A fluorescent material is provided at the distal end of the insertion portion. One end of a universal cord is coupled to an operation portion connected to the proximal end of the insertion portion. The other end of the universal cord is coupled to a processor unit. A laser light source is provided inside the processor unit. Light from the laser light source is guided to the distal end of the endoscope insertion portion through one optical fiber. When excitation light is applied to the fluorescent material, white fluorescence in which red, green, and blue fluorescences are mixed is applied.

If a light guide member is changed from a bundle fiber to one optical fiber as in Japanese Patent No. 4732783, the optical fiber may break when the light guide member is bent. In this case, it is highly possible that the amount of illumination light emitted from the distal end of the light guide member may considerably decrease. More specifically, a large number, for example, several thousand thin fibers are bundled in the bundle fiber, so that the influence on the illumination light amount is small even if several ones of a large number of optical fibers constituting the bundle fiber have broken when the bundle fiber is bent. In contrast, in the case where one optical fiber is incorporated in the insertion portion of the endoscope, if the optical fiber breaks when the optical fiber is bent, the illumination light amount reaches zero because no laser light is guided.

Particularly in the case of the endoscope having the flexible insertion portion, it is highly possible that the optical fiber may break because of buckling or pulling as a result of repeated deformation of the endoscope insertion portion into the straight state and the curved state. The optical fiber movably disposed inside the insertion portion may fit into the space between contents such as electric cables and tubes disposed around the optical fiber so that the necessary length is smaller in the curved state than in the straight state.

On the other hand, when the optical fiber is caught between contents such as electric cables and tubes disposed around the optical fiber, the necessary length is greater in the curved state than in the straight state. That is, as a result of repeated deformation of the endoscope insertion portion into the straight state and the curved state, the optical fiber inside is repeatedly compressed and pulled, which increases the possibility that the optical fiber may buckle or break.

The present invention has been made in view of the foregoing circumstances, and is intended to provide an optical fiber length adjuster capable of preventing an optical fiber from breaking when the optical fiber is disposed in a device to vary necessary length.

BRIEF SUMMARY OF THE INVENTION

An optical fiber length adjuster includes an entrance and an exit for an optical fiber, and a holding portion to hold the optical fiber so that the optical fiber is deformed. The holding portion is configured to decrease the length of the part of the optical fiber that is held, when tensile force applied to the optical fiber is increased, and increase the length of the part of the optical fiber that is held, when the tensile force applied to the optical fiber is decreased.

Advantageous Effects of Invention

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute apart of the specification, illustrate embodiments of the invention, and together with the general description given above and the detailed description of the embodiments given below, serve to explain the principles of the invention.

FIG. 1 is a diagram showing the schematic configuration of the whole endoscope equipped with an optical fiber length adjuster according to a first embodiment of the present invention;

FIG. 2 is a diagram showing the schematic configuration of the optical fiber length adjuster according to the first embodiment;

FIG. 3 is a perspective view showing a movable bobbin of the optical fiber length adjuster according to the first embodiment;

FIG. 4 is a schematic configuration diagram of the optical fiber length adjuster according to the first embodiment showing how the movable bobbin of the optical fiber length adjuster has moved;

FIG. 5 is a schematic configuration diagram showing a first modification of the optical fiber length adjuster according to the first embodiment;

FIG. 6 is a schematic configuration diagram showing a second modification of the optical fiber length adjuster according to the first embodiment;

FIG. 7 is a schematic configuration diagram showing an optical fiber length adjuster according to a second embodiment of the present invention;

FIG. 8 is a schematic configuration diagram showing an optical fiber length adjuster according to a third embodiment of the present invention;

FIG. 9 is a schematic configuration diagram of the optical fiber length adjuster according to the third embodiment showing how a movable bobbin of the optical fiber length adjuster has moved; and FIG. 10 is a schematic configuration diagram showing an optical fiber length adjuster according to a fourth embodiment of the present invention.

DETAILED DESCRIPTION OF THE INVENTION

First Embodiment (Configuration)

FIG. 1 to FIG. 4 show a first embodiment of the present invention. FIG. 1 is a diagram showing the schematic configuration of the whole endoscope 1. The endoscope 1 roughly comprises a distal end 2, an insertion portion 3, an operation portion 4, a connection portion 5, and a system box 6. The distal end 2 and the insertion portion 3 are portions to be inserted into a body. Although not shown, a unit to curve the insertion portion 3, and switches for air supply/water supply are disposed in the operation portion 4.

An illumination window (not shown) to apply illumination light and an observation window (not shown) to observe the inside of the body are provided in the distal end 2. The connection portion 5 is formed by, for example, a universal cord. The operation portion 4 and the system box 6 are connected via the connection portion 5. A laser light source 7 for illumination and a controller 8 of the image pickup device are disposed in the system box 6.

An optical fiber 9 and an electric cable 10 are provided through the insertion portion 3, the operation portion 4, the connection portion 5, and the system box 6. The proximal end of the optical fiber 9 is connected to the laser light source 7 inside the system box 6. Moreover, the optical fiber 9 extends via an optical fiber length adjuster 11 according to the present embodiment disposed in the operation portion 4.

Converting means (not shown) for converting the laser light guided through the optical fiber 9 to desired illumination light is provided inside the illumination window of the distal end 2. This converting means may be, for example, a type in which a fluorescent material is disposed to convert the laser light to white light, or a type in which a scattering member is disposed to scatter and apply the laser light. The laser light guided to the distal end 2 through the optical fiber 9 is applied to the outside from the illumination window after converted to desired illumination light by the converting means.

The image pickup device (not shown) to image an observation figure entering from the observation window is provided inside the observation window of the distal end 2. An electric signal output from the image pickup device is transmitted to the controller 8 in the system box 6 via the electric cable 10 provided in the insertion portion 3, the operation portion 4, and the connection portion 5. Although not shown here, a wire to curve the insertion portion 3, air supply/water tubes, and a tube for forceps insertion are disposed throughout the endoscope 1.

Now, details of the structure of the optical fiber length adjuster 11 according to the present embodiment are described with reference to FIG. 2 to FIG. 4. As shown in FIG. 2, the optical fiber length adjuster 11 comprises an optical fiber holding portion 14 having a half-moon fixed bobbin (contact member) 12 and a half-moon movable bobbin (contact member) 13 to be in contact with the optical fiber 9, and an entrance 15 and an exit 16 of the optical fiber 9. The entrance 15 of the optical fiber 9 is disposed on the side to connect to the insertion portion 3 of the endoscope 1. The exit 16 is disposed on the side to connect to the system box 6.

The fixed bobbin 12 is fixed to a base member 17 of the optical fiber length adjuster 11 by means such as a bolt. As shown in FIG. 3, the fixed bobbin 12 has an optical fiber pressing portion 12a comprising a half-moon circumferential surface, and a flat portion 12b cut along the diameter of the circle. One end of each of a pair of linear motion guides 18a and 18b is fixed to the flat portion 12b of the fixed bobbin 12.

The movable bobbin 13 has an optical fiber pressing portion 13a comprising a half-moon circumferential surface, and a flat portion 13b cut along the diameter of the circle. The flat portion 13b of the movable bobbin 13 is disposed to face the flat portion 12b of the fixed bobbin 12. A pair of linear motion guide insertion holes 19a and 19b are formed in the flat portion 13b of the movable bobbin 13. These linear motion guide insertion holes 19a and 19b are inserted through the linear motion guides 18a and 18b movably in their axial directions. As a result, the movable bobbin 13 is supported to be able to be in and out of contact with the fixed bobbin 12 via the linear motion guides 18a and 18b. Thus, the movable bobbin 13 is allowed to move in a crosswise direction without slide resistance in FIG. 2, but not to move in a vertical direction.

Furthermore, a coil spring (elastic member) 20 to urge the movable bobbin 13 in a direction to separate from the fixed bobbin 12 is disposed between the fixed bobbin 12 and the movable bobbin 13. When the relative distance between the fixed bobbin 12 and the movable bobbin 13 decreases, force is generated in such a direction that the fixed bobbin 12 and the movable bobbin 13 separate from each other. Instead of the coil spring 20, the elastic member may be a material such as a leaf spring or a spiral spring to generate elastic force by elastic deformation of a solid member. Otherwise, the elastic member may be a material such as an air spring that generates elastic force by the volume change of a liquid or a gas. Moreover, the elastic member may be a material such as a magnet that generates elastic force by magnetic force. The elastic member only generates elastic force in a direction in which the movement of the movable bobbin 13 is permitted by the linear motion guides 18a and 18b.

The (part of the) optical fiber 9 that is inserted in the optical fiber length adjuster 11 is set to be wound around the optical fiber pressing portion 12a of the fixed bobbin 12 and the optical fiber pressing portion 13a of the movable bobbin 13. The radiuses of the circular parts of the optical fiber pressing portion 12a of the fixed bobbin 12 and the optical fiber pressing portion 13a of the movable bobbin 13 are set to the minimum flexural radius of the optical fiber 9 such that, for example, the optical fiber 9 does not break or such that the light loss through the optical fiber 9 does not become excessively great. That is, the optical fiber pressing portions 12a and 13a comprise curved surfaces having curvatures greater than the minimum flexural radius of the optical fiber 9. Moreover, the optical fiber pressing portions 12a and 13a are lubricated (e.g. coated with a Teflon (registered trademark) resin, a DLC film) to facilitate the sliding of the optical fiber on the optical fiber pressing portions 12a and 13a.

The movable range of the movable bobbin 13 is determined by a shrinkable length of the coil spring 20, so that an optimum spring member is selected in accordance with the length adjustment amount of the optical fiber 9. The optical fiber 9 is wound around the fixed bobbin 12 and the movable bobbin 13 to make one or more loops while the coil spring 20 is shrunk to some degree.

As shown in FIG. 3, detachment prevention walls 12c and 13c having diameters larger than the diameters of the circumferential parts of the optical fiber pressing portions 12a and 13a are provided on both side portions of the optical fiber pressing portions 12a and 13a of the fixed bobbin 12 and the movable bobbin 13. The detachment prevention walls 12c and 13c prevent the optical fiber 9 from coming off the circumferential parts of the optical fiber pressing portions 12a and 13a of the fixed bobbin 12 and the movable bobbin 13.

The surface of the circumferential part of the optical fiber 9 according to the present embodiment is preferably coated with a Teflon (registered trademark) resin so that the optical fiber easily slides. The optical fiber 9 may be configured have a tube disposed on its outer circumference to facilitate its sliding on the fixed bobbin 12 and the movable bobbin 13.

(Functions)

Now, functions of the above configuration are described. In the optical fiber length adjuster 11 according to the present embodiment, the optical fiber 9 is wound one or more turns around the fixed bobbin 12 and the movable bobbin 13 of the optical fiber holding portion 14 while the coil spring 20 is shrunk to some degree. The optical fiber 9 is wound so that the coil spring 20 is shrunk in this way, and thus tensile force corresponding to the restitution of the coil spring 20 is constantly applied to the optical fiber 9. This state is an initial state.

The optical fiber length adjuster 11 operates as follows in accordance with the change in the degree of external force in a pulling direction applied to the optical fiber 9 in the insertion portion 3 of the endoscope 1. For example, during the insertion of the insertion portion 3 of the endoscope 1 into the body, the insertion portion 3 of the endoscope 1 is repeatedly deformed into a straight shape and a curved shape. At the same time, tensile force or compressive force is applied or no external force is applied to the optical fiber 9 in the insertion portion 3 suitably for the shape change of the insertion portion 3.

When the insertion portion 3 of the endoscope 1 is held in a straight state, the part of the optical fiber 9 that is wound around the fixed bobbin 12 and the movable bobbin 13 of the optical fiber holding portion 14 in the optical fiber length adjuster 11 is held in the initial state. At the same time, the length of the part of the optical fiber 9 that is inserted in the insertion portion 3 is held in a normal state.

When the insertion portion 3 of the endoscope 1 is curved into a curved shape and the optical fiber 9 is subjected to external force in the pulling direction accordingly, the movable bobbin 13 moves in a direction to approach the fixed bobbin 12 of the optical fiber holding portion 14 against the spring force of the coil spring 20 in the optical fiber length adjuster 11 as shown in FIG. 4. At the same time, the length of the part of the optical fiber 9 that is wound around the fixed bobbin 12 and the movable bobbin 13 of the optical fiber holding portion 14 decreases, so that the tensile force applied to the optical fiber 9 is kept equal to that in the initial state. Therefore, in this case, the optical fiber 9 is let out of the optical fiber length adjuster 11 toward the insertion portion 3, so that the length of the part of the optical fiber 9 that is inserted in the insertion portion 3 becomes greater than that in the normal state;

On the other hand, when the optical fiber 9 on the side of the insertion portion 3 is superfluous as a result of the curving of the insertion portion 3, the movable bobbin 13 is pressed in a direction (the rightward direction in FIG. 4) to separate from the fixed bobbin 12. At the same time, the length of the part of the optical fiber 9 that is wound around the fixed bobbin 12 and the movable bobbin 13 of the optical fiber holding portion 14 increases, so that the tensile force applied to the optical fiber 9 is kept equal to that in the initial state. Therefore, in this case, the optical fiber 9 is let into the optical fiber length adjuster 11 from the side of the insertion portion 3, so that the length of the part of the optical fiber 9 that is inserted in the insertion portion 3 becomes smaller.

Thus, even when the length of the optical fiber 9 needed on the side of the insertion portion 3 for the curving operation of, the insertion portion 3 of the endoscope 1 is changed, the length of the optical fiber 9 is adjusted by the movement of the movable bobbin 13 in the optical fiber length adjuster 11. At the same time, constant tensile force is kept generated in the optical fiber 9. That is, in response to the change of the tensile force applied to the optical fiber 9, the optical fiber holding portion 14 adjusts the length of the part of the optical fiber 9 that is held so as to keep constant tensile force applied to the optical fiber 9. Thus, the length of the part of the optical fiber 9 that is out from the entrance 15 is kept at the necessary length. As a result, it is possible to prevent excessive tensile force/compressive force from working on the optical fiber 9 during the change of the length of the optical fiber 9, and therefore prevent the optical fiber 9 from breaking/buckling.

(Advantageous Effects)

The configuration described above has the following advantageous effects. According to the present embodiment, the optical fiber length adjuster 11 to automatically adjust the length of the optical fiber 9 is provided between the insertion portion 3 of the endoscope 1 and the laser light source 7 inside the system box 6. Thus, even if the insertion portion 3 of the endoscope 1 is repeatedly deformed into the straight shape and the curved shape and the necessary length of the optical fiber 9 changes inside the insertion portion 3 of the endoscope 1, the length of the optical fiber 9 is always automatically adjusted, so that the decrease in the illumination light amount resulting from the buckling/breaking can be prevented. Consequently, it is possible to provide the optical fiber length adjuster 11 capable of preventing the optical fiber 9 from breaking when the optical fiber 9 is disposed in a device such as the insertion portion 3 of the endoscope 1 that varies necessary length.

Although the optical fiber length adjuster 11 is disposed in the operation portion 4 in the configuration shown according to the present embodiment, the optical fiber length adjuster 11 does not always need to be disposed in the operation portion 4. Similar advantageous effects can be obtained if the optical fiber length adjuster 11 is disposed in the distal end 2, the insertion portion 3, the connection portion 5, or the system box 6.

Furthermore, when a wider length adjustment range of the optical fiber 9 is needed, the optical fiber 9 can be wound around the fixed bobbin 12 and the movable bobbin 13 two or more turns rather than one turn.

Although the two linear motion guides 18a and 18b are arranged at symmetrical portions according to the present embodiment, only one linear motion guide may be disposed in the center. In this case, the rotation of the movable bobbin 13 about its axis can be prevented if the section of the linear motion guide is formed into a noncircular shape rather than a circular shape. That is, the linear motion guides 18a and 18b according to the present embodiment are linear guides, and regulate the movement directions of the fixed bobbin 12 and the movable bobbin 13 to one linear direction and also have a function of reducing slide resistance in one direction to be permitted.

[First Modification]
(Configuration)

FIG. 5 is a schematic configuration diagram showing a first modification of the optical fiber length adjuster 11 according to the first embodiment (see FIG. 1 to FIG. 4). In the present modification, a fixing portion 21 is provided to fix the insertion part of the optical fiber 9 to be inserted through the exit 16 of the optical fiber length adjuster 11 by, for example, an adhesive agent.

(Functions, Advantageous Effects)

In the present modification, necessary length can be changed only in the optical fiber 9 on the side of the insertion portion 3 of the endoscope 1 by the optical fiber length adjuster 11. Therefore, the length of the optical fiber 9 on the side of the insertion portion 3 of the endoscope 1 can be more effectively adjusted.

[Second Modification]
(Configuration)

FIG. 6 is a schematic configuration diagram showing a second modification of the optical fiber length adjuster 11 according to the first embodiment (see FIG. 1 to FIG. 4). In the present modification, each of two bobbins (contact members) 22a and 22b of the optical fiber holding portion 14 of the optical fiber length adjuster 11 is changed to a movable bobbin. The two movable bobbins 22a and 22b have the same configuration as the movable bobbin 13 according to the first embodiment. A pair of linear motion guide insertion holes 23a and 23b are formed in each of the movable bobbins 22a and 22b. Linear motion guides 24a and 24b are movably inserted through the linear motion guide insertion holes 23a and 23b in their axial directions. The linear motion guides 24a and 24b are provided to protrude in, for example, the base member 17 of the optical fiber length adjuster 11. As a result, the movable bobbins 22a and 22b are supported to be able to be in and out of contact with each other via the linear motion guides 24a and 24b. Thus, the movable bobbins 22a and 22b are allowed to move in a crosswise direction without slide resistance in FIG. 6, but not to move in a vertical direction.

(Functions, Advantageous Effects)

In the present modification as well, advantageous effects similar to those according to the first embodiment can be obtained. Moreover, in the present modification, the two movable bobbins 22a and 22b can be shaped to have the same structure, so that the configuration can be simpler.

[Third Modification]
(Configuration)

FIG. 7 shows a second embodiment of the present invention. An optical fiber length adjuster 31 according to the present embodiment is provided with a half-moon first movable bobbin (contact member) 33 to be in contact with an optical fiber 9, which is inserted into a housing 32 of the optical fiber length adjuster 31, from the upper side in FIG. 7, and a half-moon second movable bobbin (contact member) 34 to be in contact with the optical fiber 9 from the lower side in FIG. 7. The first movable bobbin 33 and the second movable bobbin 34 are staggered across the optical fiber 9 to form an optical fiber holding portion 35.

The first movable bobbin 33 has an optical fiber pressing portion 33a comprising a semicircular circumferential surface, and a flat portion 33b cut along the diameter of the circle. A pair of linear motion guide insertion holes 33c and 33c are formed in the flat portion 33b of the first movable bobbin 33. Two parallel linear motion guides 36a and 36b vertically extending in FIG. 7 are movably inserted through the linear motion guide insertion holes 33c and 33c in their axial directions. The two linear motion guides 36a and 36b are provided to protrude in a top plate 37 of the housing 32. A coil spring (elastic member) 38 to urge the first movable bobbin 33 in a direction to separate from the top plate 37 is disposed between the top plate 37 of the housing 32 and the flat portion 33b of the first movable bobbin 33. When the relative distance between the first movable bobbin 33 and the top plate 37 decreases, force is generated in such a direction that the first movable bobbin 33 separates from the top plate 37.

The second movable bobbin 34 is similar in configuration to the first movable bobbin 33. That is, the second movable bobbin 34 has an optical fiber pressing portion 34a comprising a semicircular circumferential surface, and a flat portion 34b cut along the diameter of the circle. A pair of linear motion guide insertion holes 34c and 34c are formed in the flat portion 34b of the second movable bobbin 34. Two parallel linear motion guides 39a and 39b vertically extending in FIG. 7 are movably inserted through the linear motion guide insertion holes 34c and 34c in their axial directions. The two linear motion guides 39a and 39b are provided to protrude in a lower plate 40 of the housing 32. A coil spring (elastic member) 41 to urge the second movable bobbin 34 in a direction to separate from the lower plate 40 is disposed between the lower plate 40 of the housing 32 and the flat portion 34b of the second movable bobbin 34. When the relative distance between the second movable bobbin 34 and the lower plate 40 decreases, force is generated in such a direction that the second movable bobbin 34 separates from the lower plate 40.

(Functions)

Now, functions of the above configuration are described. In the optical fiber length adjuster 31 according to the present embodiment, the optical fiber pressing portion 33a of the first movable bobbin 33 contacts the optical fiber 9, which is inserted into the housing 32, from the upper side in FIG. 7, and the optical fiber pressing portion 34a of the second movable bobbin 34 contacts the optical fiber 9 from the lower side in FIG. 7. Thus, the optical fiber 9 in the housing 32 is held in such a manner as to be deformed into a substantially S-shape as shown in FIG. 7. At the same time, the coil spring 38 of the first movable bobbin 33 and the coil spring 41 of the second movable bobbin 34 are held in a shrunk state by press force from the optical fiber 9, and thus tensile force corresponding to the restitution of the coil springs 38 and 41 is constantly applied to the optical fiber 9. This state is an initial state.

The optical fiber length adjuster 31 operates as follows in accordance with the change in the degree of external force in a pulling direction applied to the optical fiber 9 in the insertion portion 3 of the endoscope 1. When the insertion portion 3 of the endoscope 1 is held in a straight state, the optical fiber 9 in the optical fiber length adjuster 31 is held in the initial state to be deformed into a substantially S-shape by the first movable bobbin 33 and the second movable bobbin 34 of the optical fiber holding portion 35. At the same time, the length of the part of the optical fiber 9 that is inserted in the insertion portion 3 is held in a normal state.

When the insertion portion 3 of the endoscope 1 is curved into a curved shape and the optical fiber 9 is subjected to external force in the pulling direction accordingly, the first movable bobbin 33 moves in such a direction that the relative distance between the first movable bobbin 33 and the top plate 37 decreases against the spring force of the coil spring 38, while the second movable bobbin 34 moves in such a direction that the relative distance between the second movable bobbin 34 and the lower plate 40 decreases against the spring force of the coil spring 41, in the optical fiber length adjuster 31. At the same time, the optical fiber 9 in the optical fiber length adjuster 31 is deformed in such a direction that the curving degree of the S-shape formed as a result of the pressure by the first movable bobbin 33 and the second movable bobbin 34 of the optical fiber holding portion 35 becomes lower, and the optical fiber 9 is deformed into a straight linear state. When the length of the part of the optical fiber 9 that is inserted in the housing 32 of the optical fiber length adjuster 31 is decreased, the tensile force applied to the optical fiber 9 is kept equal to that in the initial state. Therefore, in this case, the optical fiber 9 is let out of the optical fiber length adjuster 31 toward the insertion portion 3, so that the length of the part of the optical fiber 9 that is inserted in the insertion portion 3 becomes greater than that in the normal state.

On the other hand, when the optical fiber 9 on the side of the insertion portion 3 is superfluous as a result of the curving of the insertion portion 3, the first movable bobbin 33 moves in such a direction that the relative distance between the first movable bobbin 33 and the top plate 37 increases due to the spring force of the coil spring 38, while the second movable bobbin 34 moves in such a direction that the relative distance between the second movable bobbin 34 and the lower plate 40 increases due to the spring force of the coil spring 41, in the optical fiber length adjuster 31. At the same time, the optical fiber 9 in the optical fiber length adjuster 31 is deformed in such a direction that the curving degree of the S-shape formed as a result of the pressure by the first movable bobbin 33 and the second movable bobbin 34 of the optical fiber holding portion 35 becomes higher. When the length of the part of the optical fiber 9 that is inserted in the housing 32 of the optical fiber length adjuster 31 is increased, the tensile force applied to the optical fiber 9 is kept equal to that in the initial state. Therefore, in this case, the optical fiber 9 islet into the optical fiber length adjuster 31 from the side of the insertion portion 3, so that the length of the part of the optical fiber 9 that is inserted in the insertion portion 3 becomes smaller.

Thus, even when the length of the optical fiber 9 needed on the side of the insertion portion 3 for the curving operation of the insertion portion 3 of the endoscope 1 is changed, the length of the optical fiber 9 is adjusted by the movement of the first movable bobbin 33 and the second movable bobbin 34 in the optical fiber length adjuster 31. At the same time, constant tensile force is kept generated in the optical fiber 9. That is, in response to the change of the tensile force applied to the optical fiber 9, the optical fiber holding portion 35 adjusts the length of the part of the optical fiber 9 that is held so as to keep constant tensile force applied to the optical fiber 9. Thus, the length of the part of the optical fiber 9 that is out from the entrance is kept at the necessary length. As a result, it is possible to prevent excessive tensile force/compressive force from working on the optical fiber 9 during the change of the length of the optical fiber 9, and therefore prevent the optical fiber 9 from breaking/buckling.

(Advantageous Effects)

According to the present embodiment, even if the insertion portion 3 of the endoscope 1 is repeatedly deformed into the straight shape and the curved shape and the necessary length of the optical fiber 9 changes inside the insertion portion 3 of the endoscope 1, the length of the optical fiber 9 is always automatically adjusted by the optical fiber length adjuster 31, so that the decrease in the illumination light amount resulting from the buckling/breaking of the optical fiber 9 can be prevented. Consequently, advantageous effects similar to those obtained by the optical fiber length adjuster 11 according to the first embodiment can also be obtained by the optical fiber length adjuster 31 according to the present embodiment. Moreover, the first movable bobbin 33 and the second movable bobbin 34 are staggered across the optical fiber 9 in the optical fiber length adjuster 31 according to the present embodiment, so that the housing 32 of the optical fiber length adjuster 31 can be designed to be elongated.

Although two press units for the optical fiber 9 each composing the movable bobbin, the two linear motion guides, and the coil spring are provided according to the present embodiment, three or more press units may be provided. Moreover, more than one bobbin may move together. For example, two first movable bobbins 33 may be disposed on the top plate 37 of the housing 32, and two second movable bobbins 34 may be disposed on the lower plate 40, so that the two first movable bobbins 33 on the top plate 37 may be allowed to move together, and the two second movable bobbins 34 on the lower plate 40 may be allowed to move together.

Third Embodiment (Configuration)

FIG. 8 and FIG. 9 show a third embodiment of the present invention. An optical fiber length adjuster 51 according to the present embodiment is provided with a large number of half-moon movable bobbins, in the present embodiment, eight movable bobbins 52 to be in contact with an optical fiber 9 from the inside. A spiral spring 53 is provided in the optical fiber length adjuster 51. The spiral spring 53 is fixed to a base member 51a constituting the housing of the optical fiber length adjuster 51 in the center. Eight radially extending linear motion guides 54 are substantially equally spaced out in the spiral spring 53 along the circumferential direction of the spiral spring 53. The inner end of each of the linear motion guides 54 is fixed to the base member 51a.

Each movable bobbin 52 has an optical fiber pressing portion 52a comprising a semicircular circumferential surface, and a flat portion 52b cut along the diameter of the circle. One linear motion guide insertion hole 55 is formed in the center of the flat portion 52b of the movable bobbin 52. The linear motion guide insertion hole 55 of each movable bobbin 52 is inserted through the linear motion guide 54 movably in its axial direction. As a result, each movable bobbin 52 is supported movably inward and outward along the linear motion guide 54. The outer circumferential part of the spiral spring 53 is in contact with the flat portion 52b of each movable bobbin 52.

The optical fiber 9 inserted in the optical fiber length adjuster 51 is wound to make one or more loops connecting the tops of the outer circumferential surfaces of the optical fiber pressing portions 52a of the eight movable bobbins 52. In this instance, the optical fiber 9 is wound one or more turns while the spiral spring 53 is shrunk to some degree. The optical fiber 9 is wound while the spiral spring 53 is shrunk in this way, and thus tensile force corresponding to the restitution of the spiral spring 53 is constantly applied to the optical fiber 9. This state is an initial state.

(Functions)

Now, functions of the above configuration are described. In the optical fiber length adjuster 51 according to the present embodiment, when the insertion portion 3 of the endoscope 1 is held in a straight state, the optical fiber 9 wound to connect the tops of the outer circumferential surfaces of the optical fiber pressing portions 52a of the eight movable bobbins 52 in the optical fiber length adjuster 51 is held in the initial state. At the same time, the length of the part of the optical fiber 9 that is inserted in the insertion portion 3 is held in a normal state.

When the insertion portion 3 of the endoscope 1 is curved into a curved shape and the optical fiber 9 is subjected to external force in the pulling direction accordingly, press force from the optical fiber 9 works in a direction to decrease the diameter of the loop connecting the tops of the outer circumferential surfaces of the optical fiber pressing portions 52a of the eight movable bobbins 52 against the spring force of the spiral spring 53 as shown in FIG. 8, in the optical fiber length adjuster 51 according to the present embodiment. At the same time, the eight movable bobbins 52 move inward along the linear motion guide 54. As a result, the optical fiber 9 is deformed in the direction to decrease the diameter of the loop of the optical fiber 9 connecting the tops of the outer circumferential surfaces of the optical fiber pressing portions 52a of the eight movable bobbins 52, and the length of the optical fiber 9 in the optical fiber length adjuster 51 decreases accordingly, so that the tensile force applied to the optical fiber 9 is kept equal to that in the initial state. Therefore, in this case, the optical fiber 9 is let out of the optical fiber length adjuster 51 toward the insertion portion 3, so that the length of the part of the optical fiber 9 that is inserted in the insertion portion 3 becomes greater than that in the normal state.

On the other hand, when the optical fiber 9 on the side of the insertion portion 3 is superfluous as a result of the curving of the insertion portion 3, the press force to press the eight movable bobbins 52 from the optical fiber 9 in the optical fiber length adjuster 51 decreases. Therefore, the eight movable bobbins 52 move outward along the linear motion guide 54 as shown in FIG. 9 in response to the spring force of the spiral spring 53. As a result, the optical fiber 9 is deformed in the direction to increase the diameter of the loop of the optical fiber 9 connecting the tops of the outer circumferential surfaces of the optical fiber pressing portions 52a of the eight movable bobbins 52, and the length of the optical fiber 9 in the optical fiber length adjuster 51 increases accordingly, so that the tensile force applied to the optical fiber 9 is kept equal to that in the initial state. Therefore, in this case, the optical fiber 9 is let into the optical fiber length adjuster 51 from the side of the insertion portion 3, so that the length of the part of the optical fiber 9 that is inserted in the insertion portion 3 becomes smaller.

Thus, even when the length of the optical fiber 9 needed on the side of the insertion portion 3 for the curving operation of the insertion portion 3 of the endoscope 1 is changed, the length of the optical fiber 9 is adjusted by the movement of the movable bobbins 52 in the optical fiber length adjuster 51. In response to the change of the tensile force applied to the optical fiber 9, the optical fiber holding portion including the eight movable bobbins 52 adjusts the length of the part of the optical fiber 9 that is held so as to keep constant tensile force applied to the optical fiber 9. Thus, the length of the part of the optical fiber 9 that is out from the entrance is kept at the necessary length. As a result, constant tensile force is kept generated in the optical fiber 9 at the same time. That is, it is possible to prevent excessive tensile force/compressive force from working on the optical fiber 9 during the change of the length of the optical fiber 9, and therefore prevent the optical fiber 9 from breaking/buckling.

(Advantageous Effects)

According to the present embodiment, even if the insertion portion 3 of the endoscope 1 is repeatedly deformed into the straight shape and the curved shape and the necessary length of the optical fiber 9 changes inside the insertion portion 3 of the endoscope 1, the length of the optical fiber 9 is always automatically adjusted by the optical fiber length adjuster 51, so that the decrease in the illumination light amount resulting from the buckling/breaking of the optical fiber 9 can be prevented. Consequently, it is possible to provide the optical fiber length adjuster 51 capable of preventing the optical fiber 9 from breaking when the optical fiber 9 is disposed in a device such as the insertion portion 3 of the endoscope 1 that varies necessary length. Moreover, according to the present embodiment, even if the linear motion guide 54 is short and the movable amount of each of the eight movable bobbins 52 is small, the length adjustment amount of the optical fiber 9 can be greater. The circular arc part of the optical fiber pressing portion 52a of the movable bobbin 52 may be in the shape of a fan of 180° or less. Moreover, the loop of the optical fiber 9 may be elliptic.

Fourth Embodiment (Configuration)

FIG. 10 shows a fourth embodiment of the present invention. An optical fiber length adjuster 61 according to the present embodiment has a spiral spring 62, a rotation shaft 63 having one end fixed to the center of the spiral spring 62, and a discoid rotary bobbin 64 fixed to the other end of the rotation shaft 63. The end of the spiral spring 62 on its outer circumferential side is fixed to a base member 61a constituting the housing of the optical fiber length adjuster 61. The other end of the rotation shaft 63 is fixed to the center of the rotary bobbin 64. The rotation shaft 63 is rotatably held by, for example, an unshown bearing.

The rotary bobbin 64 has an optical fiber pressing portion 64a comprising a circular circumferential surface, and a substantially S-shaped optical fiber receiving groove 64b formed in the end face of a circular plate. The optical fiber 9 inserted in the optical fiber length adjuster 61 is inserted into the S-shaped optical fiber receiving groove 64b of the rotary bobbin 64, and is set to be wound along the optical fiber pressing portion 64a on the circular circumferential surface from both ends of the optical fiber receiving groove 64b.

In the optical fiber length adjuster 61 according to the present embodiment, the rotary bobbin 64 is rotatable about the rotation shaft 63 in a direction about the axis. The spiral spring 62 is set to be deformed in a compressing (diameter decreasing) direction when the rotary bobbin 64 rotates about the rotation shaft 63 clockwise in FIG. 10. The spiral spring 62 is set to be deformed in an expanding (diameter increasing) direction when the rotary bobbin 64 rotates about the rotation shaft 63 counterclockwise in FIG. 10.

(Functions)

Now, functions of the above configuration are described. In the optical fiber length adjuster 61 according to the present embodiment, the optical fiber 9 is inserted into the S-shaped optical fiber receiving groove 64b of the rotary bobbin 64, and is set to be wound along the optical fiber pressing portion 64a on the circular circumferential surface from both ends of the optical fiber receiving groove 64b. In this state, the spiral spring 62 is held in a shrunk state by the press force from the optical fiber 9, and thus tensile force corresponding to the restitution of the spiral spring 62 is constantly applied to the optical fiber 9. This state is an initial state.

The optical fiber length adjuster 61 operates as follows in accordance with the change in the degree of external force in a pulling direction applied to the optical fiber 9 in the insertion portion 3 of the endoscope 1. When the insertion portion 3 of the endoscope 1 is held in a straight state, the optical fiber 9 in the optical fiber length adjuster 61 is held in the initial state. At the same time, the length of the optical fiber 9 inserted in the insertion portion 3 is held in a normal state.

When the insertion portion 3 of the endoscope 1 is curved into a curved shape and the optical fiber 9 is subjected to external force in the pulling direction accordingly, the rotary bobbin 64 rotates about the rotation shaft 63 counterclockwise in FIG. 10 against the spring force of the spiral spring 62 in the optical fiber length adjuster 61. In response to the rotation of the rotary bobbin 64, the optical fiber 9 in the optical fiber length adjuster 61 is drawn into the optical fiber length adjuster 61 from the part connected to the system box 6, and the optical fiber 9 is let out of the optical fiber length adjuster 61 toward the insertion portion 3. At the same time, the spiral spring 62 is deformed in the expanding (diameter decreasing) direction, so that the tensile force applied to the optical fiber 9 is kept equal to that in the initial state. Therefore, in this case, the optical fiber 9 is let out of the optical fiber length adjuster 61 toward the insertion portion 3, so that the length of the part of the optical fiber 9 that is inserted in the insertion portion 3 becomes greater than that in the normal state.

On the other hand, when the optical fiber 9 on the side of the insertion portion 3 is superfluous as a result of the curving of the insertion portion 3, the rotary bobbin 64 rotates about the rotation shaft 63 clockwise in FIG. 10 in accordance with the spring force of the spiral spring 62 in the optical fiber length adjuster 61. In response to the rotation of the rotary bobbin 64, the optical fiber 9 is drawn into the optical fiber length adjuster 61 from the side of the insertion portion 3. Therefore, in this case, the optical fiber 9 is let into the optical fiber length adjuster 61 from the side of the insertion portion 3, so that the length of the part of the optical fiber 9 that is inserted in the insertion portion 3 becomes smaller.

Thus, even when the length of the optical fiber 9 needed on the side of the insertion portion 3 for the curving operation of the insertion portion 3 of the endoscope 1 is changed as in the present embodiment, the length of the optical fiber 9 is adjusted by the movement of the rotary bobbin 64 in the optical fiber length adjuster 61. At the same time, constant tensile force is kept generated in the optical fiber 9. That is, in response to the change of the tensile force applied to the optical fiber 9, the optical fiber holding portion including the rotary bobbin 64 adjusts the length of the part of the optical fiber 9 that is held to keep constant tensile force applied to the optical fiber 9. Thus, the length of the part of the optical fiber 9 that is out from the entrance is kept at the necessary length. As a result, it is possible to prevent excessive tensile force/compressive force from working on the optical fiber 9 during the change of the length of the optical fiber 9, and therefore prevent the optical fiber 9 from breaking/buckling.

(Advantageous Effects)

According to the present embodiment; even if the insertion portion 3 of the endoscope 1 is repeatedly deformed into the straight shape and the curved shape and the necessary length of the optical fiber 9 changes inside the insertion portion 3 of the endoscope 1, the length of the optical fiber 9 is always automatically adjusted by the optical fiber length adjuster 61, so that the decrease in the illumination light amount resulting from the buckling/breaking of the optical fiber 9 can be prevented. Consequently, it is possible to provide the optical fiber length adjuster 61 capable of preventing the optical fiber 9 from breaking when the optical fiber 9 is disposed in a device such as the insertion portion 3 of the endoscope 1 that varies necessary length. Moreover, in the configuration of the optical fiber length adjuster 61 according to the present embodiment, the optical fiber 9 is inserted into the S-shaped optical fiber receiving groove 64b of the rotary bobbin 64, and is configured to be wound along the optical fiber pressing portion 64a on the circular circumferential surface from both ends of the optical fiber receiving groove 64b, so that the length adjustment amount of the optical fiber 9 can be much greater. Moreover, the optical fiber 9 does not need to slide on the circumferential surface of the rotary bobbin 64, and the optical fiber 9 may be fixed on the rotary bobbin 64.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope comprising:
   an insertion portion for insertion into a body to be observed;
   an optical fiber provided through the insertion portion, the optical fiber being configured to guide light from a light source to a distal end of the insertion portion; and
   an optical fiber length adjuster comprising:
   a holding portion to hold the optical fiber, and
   an entrance and an exit for the optical fiber,
   wherein the optical fiber length adjuster being configured to adjust a length of a portion of the optical fiber positioned in the insertion portion in response to a curving operation of the insertion portion;
   the optical fiber length adjuster being located between the insertion portion of the endoscope and the light source, and
   the optical fiber length adjuster adjusting the length of the portion of the optical fiber positioned in the insertion portion resulting from the curving operation of the insertion portion of the endoscope, the optical fiber length adjuster being configured to adjust the length so as to suppress an external force applied to the optical fiber resulting from the curving operation where the length changes so as to increase the length of the portion of the optical fiber positioned in the insertion portion when the optical fiber held by the holding portion receives the external force in a pulling direction of the optical fiber, and to decrease the length of the portion of the optical fiber positioned in the insertion portion when the optical fiber held by the holding portion does not receive the external force in the pulling direction of the optical fiber.

2. The endoscope according to claim 1, wherein when the length of the portion of the optical fiber changes, the optical fiber is caused to enter and exit at both the entrance and the exit for the optical fiber.

3. The endoscope according to claim 1, wherein when the length of the portion of the optical fiber changes, the optical fiber is caused to enter and exit at only the entrance for the optical fiber alone.

4. The endoscope according to claim 1, wherein the holding portion comprises
   a contact member to be in contact with the optical fiber, and
   an elastic member disposed to be coupled to the contact member,
   wherein a tensile force generated in the optical fiber via the contact member is kept constant by an elastic force generated from the elastic member, and
   the contact member moves to deform a part of the optical fiber that is held onto the contact member, so that the length of the portion of the optical fiber changes.

5. The endoscope according to claim 4, wherein the contact member has an optical fiber pressing portion having a curved surface higher in curvature than the minimum flexural radius of the optical fiber.

6. The endoscope according to claim 5, wherein the contact member includes a portion coupled to a linear motion guide, so that the contact member is allowed to move without resistance along the linear motion guide only in a direction in which the elastic member presses the contact member.

7. The endoscope according to claim 6, wherein the contact member comprises one or more half-moon members.

8. The endoscope according to claim 7, wherein the optical fiber is wound around the contact member so as to make one or more loops.

9. The endoscope according to claim 5, wherein the contact member is coupled to a rotary member allowed to rotate about a rotation axis, and
   the elastic member comprises a spring member to provide elastic force in a direction against the rotation of the rotary member during the rotation of the rotary member.

10. The endoscope according to claim 9, wherein the contact member comprises fan-shaped protrusions formed on a base portion.

11. The endoscope according to claim 5, wherein the optical fiber pressing portion includes a lubricating portion formed on a surface to be in contact with the optical fiber to facilitate the sliding of the optical fiber on the optical fiber pressing portion.

12. The endoscope according to claim 5, wherein the optical fiber pressing portion is provided with a detachment prevention wall to prevent the optical fiber from coming off a surface to be in contact with the optical fiber.

\* \* \* \* \*